(12) United States Patent
Harrison et al.

(10) Patent No.: US 7,097,651 B2
(45) Date of Patent: Aug. 29, 2006

(54) EMBOLIC PROTECTION BASKET

(75) Inventors: William J. Harrison, Temecula, CA (US); Anuja H. Patel, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/948,335

(22) Filed: Sep. 6, 2001

(65) Prior Publication Data

US 2003/0045898 A1    Mar. 6, 2003

(51) Int. Cl.
*A61M 29/00* (2006.01)
(52) U.S. Cl. .................................................. 606/200
(58) Field of Classification Search ................ 606/200, 606/110, 113, 114; 623/1.12, 1.15, 1.18, 623/1.19, 1.23
See application file for complete search history.

(56) References Cited

U.S. PATENT DOCUMENTS

| | | | |
|---|---|---|---|
| 4,494,531 A * | 1/1985 | Gianturco | 606/200 |
| 4,793,348 A * | 12/1988 | Palmaz | 606/194 |
| 5,234,458 A * | 8/1993 | Metais | 606/200 |
| 5,776,162 A * | 7/1998 | Kleshinski | 623/1.18 |
| 6,152,932 A * | 11/2000 | Ternstrom | 606/114 |
| 6,245,101 B1 * | 6/2001 | Drasler et al. | 623/1.15 |
| 6,383,196 B1 * | 5/2002 | Leslie et al. | 606/114 |
| 6,416,543 B1 * | 7/2002 | Hilaire et al. | 623/1.16 |
| 6,443,972 B1 * | 9/2002 | Bosma et al. | 606/200 |
| 6,511,496 B1 * | 1/2003 | Huter et al. | 606/200 |
| 6,726,701 B1 | 4/2004 | Gilson et al. | |

\* cited by examiner

*Primary Examiner*—Julian W. Woo
*Assistant Examiner*—Victor Nguyen
(74) *Attorney, Agent, or Firm*—Fulwider Patton LLP

(57) ABSTRACT

A basket for an embolic protection filtering device to be deployed within a body lumen for capturing embolic debris is disclosed. In one embodiment, a strut pattern forming the basket includes V-shaped struts having an internal radius at the apex with a kerf on each strut arm beginning at the radius and extending toward an opposite end of the strut. The apex may have a bulbous shape. In another embodiment, the strut arms of the basket include undulations. Also, the apices may be situated so that one apex is longitudinally staggered from an adjacent apex. The combination of features enables the basket to be crimped to a small profile while distributing stress away from the apices of the V's in the strut pattern.

40 Claims, 3 Drawing Sheets

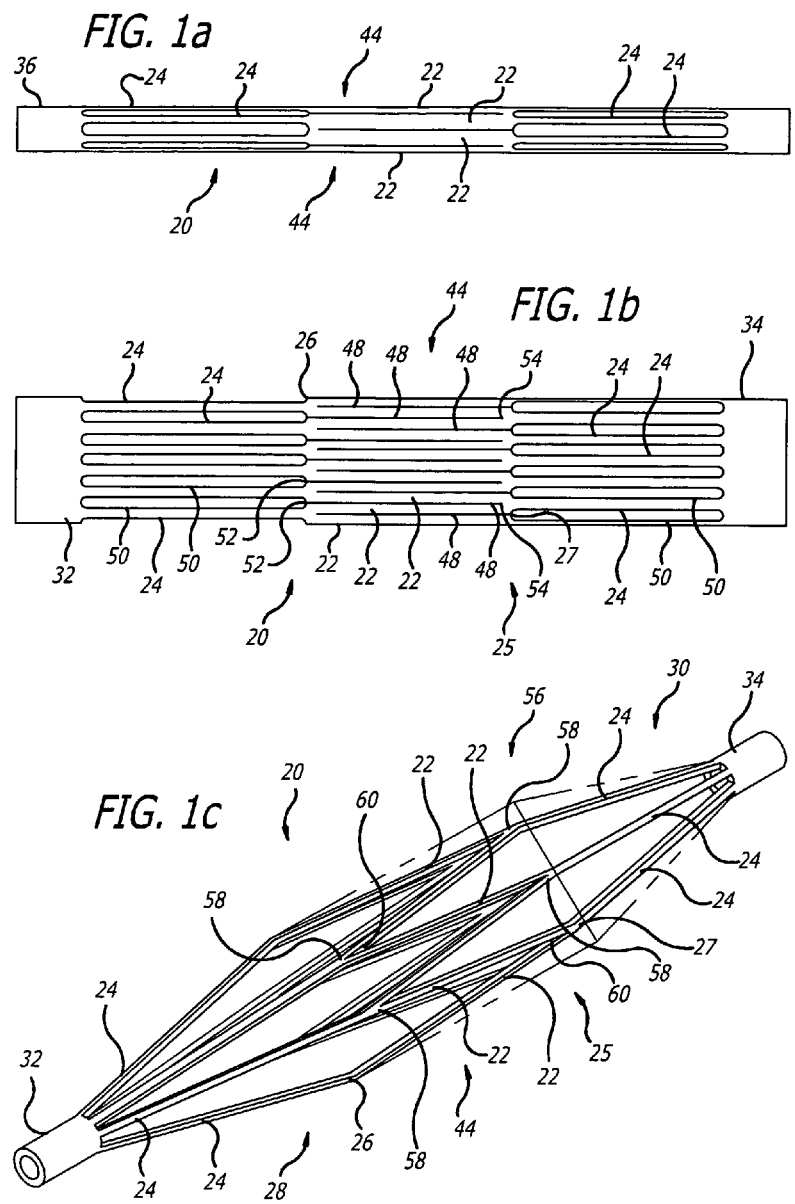

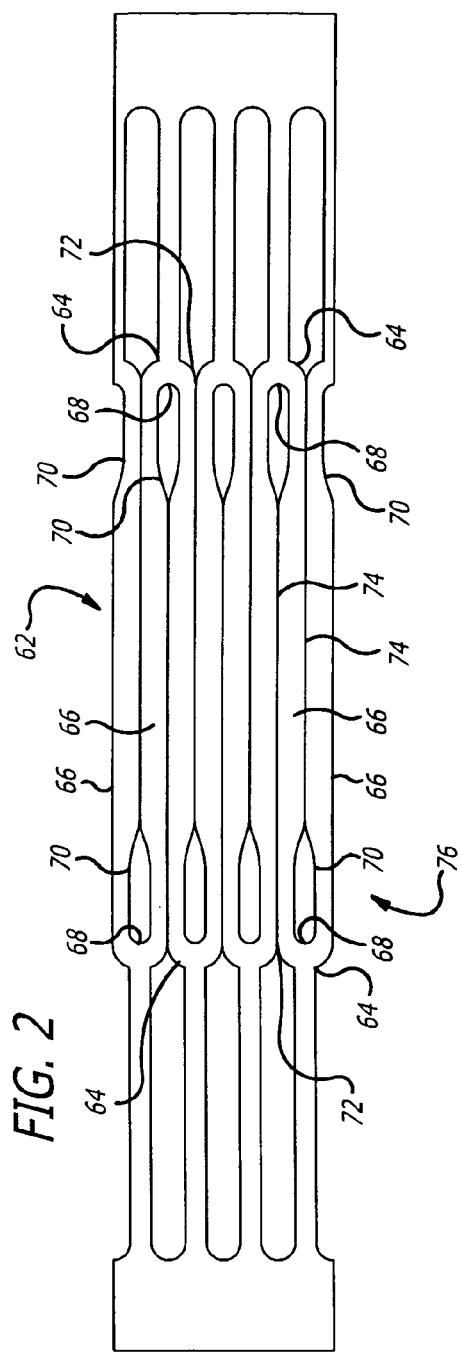
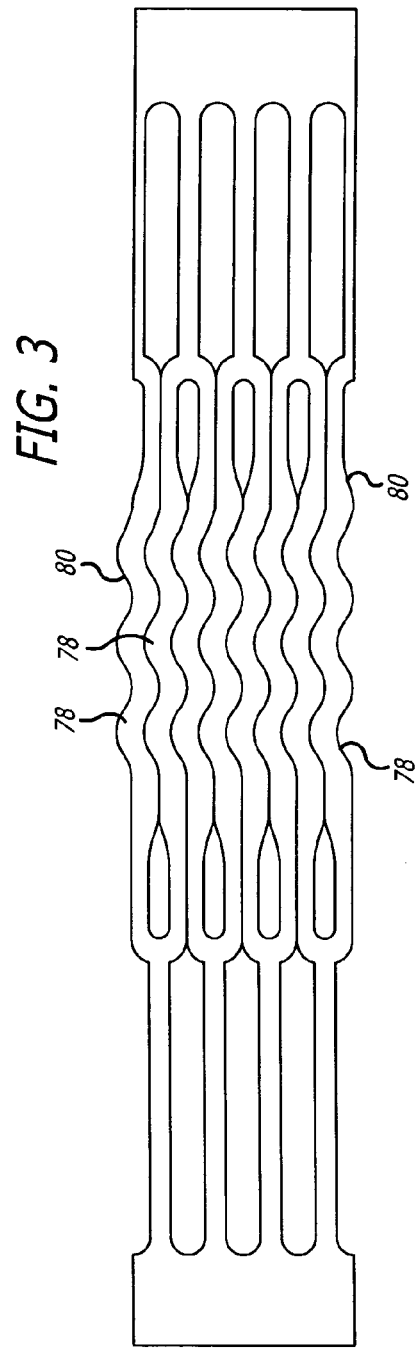

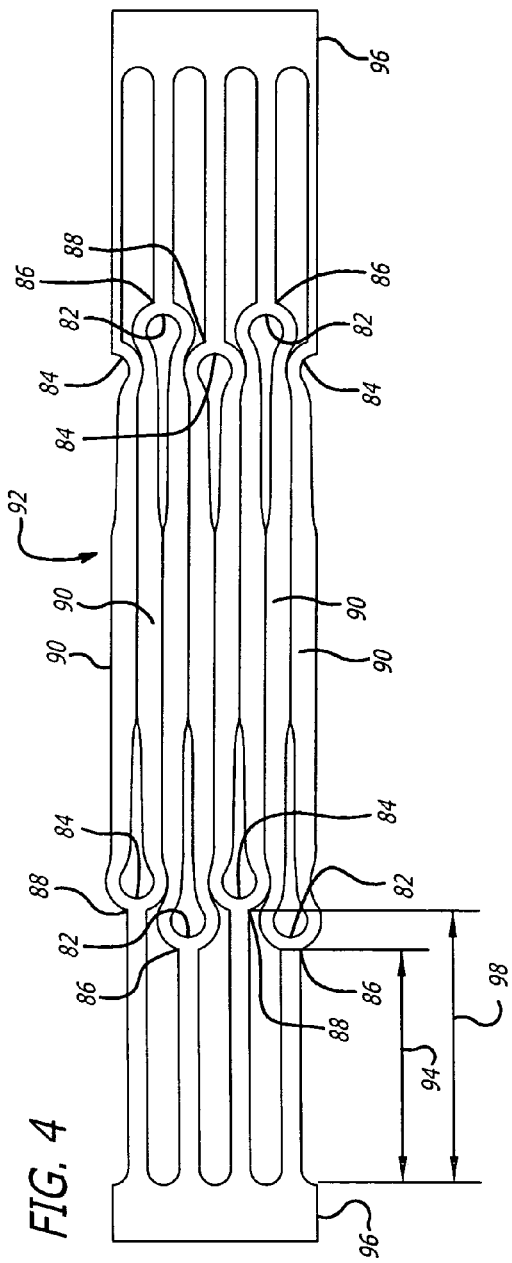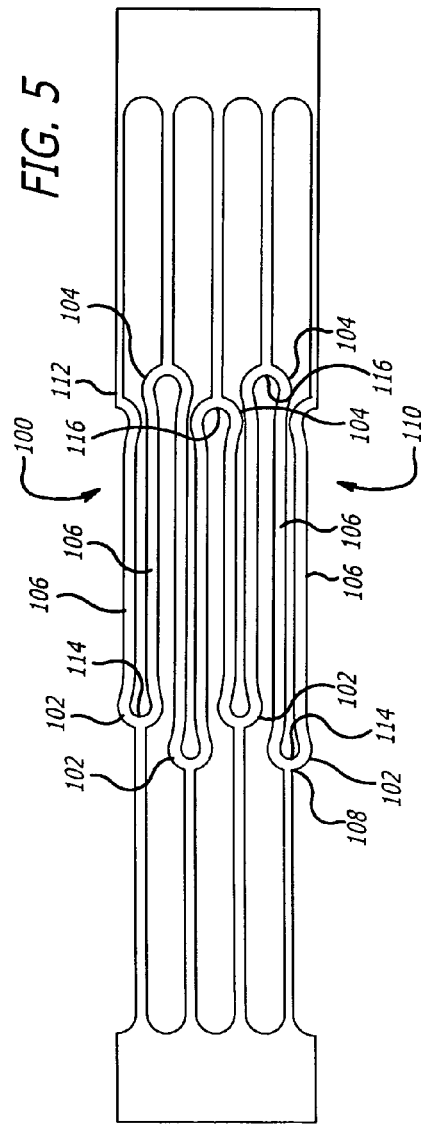

EMBOLIC PROTECTION BASKET

BACKGROUND OF THE INVENTION

The present invention relates generally to a device that can be used during an interventional procedure in a stenosed or occluded region of a blood vessel to capture embolic material that might be created and released into the bloodstream as a result of the procedure. The present invention is particularly useful when performing balloon angioplasty, stenting, laser angioplasty, or atherectomy procedures in critical vessels of a patient's body, such as the carotid arteries, where the release of embolic debris into the bloodstream can occlude the flow of oxygenated blood to the brain. The consequences to the patient of such an event are devastating.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which uses a laser to ablate the stenosis by super heating and vaporizing the deposited plaque. Atherectomy is yet another method of treating a stenosed blood vessel in which a rotating cutting blade shaves the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the diseased segment of blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA), or removal by atherectomy or other means. A stent is usually delivered in a compressed condition to the target site where it is deployed in an expanded condition to support the vessel and to help maintain patency of the lumen.

Prior art stents typically fall into two general categories of construction. The first type of stent is expandable upon application of a controlled force, often through the inflation of the balloon portion of a dilatation catheter that expands the compressed stent to a larger diameter to be left in place within the artery at the target site. The second type of stent is a self-expanding stent formed from, for example, shape memory metals or superelastic nickel-titanum (NiTi) alloys, that self-expands from a compressed state when the stent is advanced out of the distal end of the delivery catheter into the body lumen. The self-expansion of a NiTi stent is triggered either through thermally induced shape memory effect or by the stent's own superelastic properties.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque, which become embolic debris that travel downstream and lodge somewhere in the patient's vascular system. While not a frequent occurrence, pieces of plaque can sometimes dislodge from the stenosis during a balloon angioplasty procedure and become released into the bloodstream. Additionally, while complete vaporization of plaque is the intended goal during a laser angioplasty procedure, quite often the particles are not fully vaporized and enter the bloodstream. Likewise, emboli created during an atherectomy procedure may enter the bloodstream.

When any of the above-described procedures are performed in the carotid arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment using any one of the above-identified procedures. One approach that has been attempted is cutting the debris into minute sizes which pose little chance of becoming occluded in major vessels within the patient's vasculature. Yet it is often difficult to control the size of the fragments that are formed, and the risk of vessel occlusion still exists.

Other techniques that have been developed to address the problem of removing embolic debris include the use of catheters with a vacuum source that provides temporary suction to remove embolic debris from the bloodstream. On the other hand, complications exist with such systems because the vacuum catheter may not remove all of the embolic material from the bloodstream, and a more powerful suction could cause problems to the patient's vasculature.

Still other techniques that have had success include the placement of a filter assembly downstream from the treatment site to capture embolic debris before it reaches the smaller blood vessels downstream. The filter assembly is typically attached to the distal end of an elongated shaft or guide wire and is delivered to the deployment site via a delivery catheter. Such filters have proven successful in capturing embolic debris released into the bloodstream during treatment. Nevertheless, some filter assembly designs are difficult and/or time consuming to manufacture.

Some existing embolic protection filters include a filter membrane and a basket or cage that supports the filter membrane. The basket can be fabricated from a longitudinal, small diameter hypotube by cutting a particular pattern into the hypotube thus forming the struts, ribs, or framework of the basket. The hypotube can be set to a particular expanded size using successive heat treatments. The heat treatments also relieve stress that can build up in the strut pattern particularly at locations where two or more struts or ribs are joined. Without the heat treatments, the basket can fracture because of the buildup of stress at that joint or at other key areas. Unfortunately, the successive heat treatments add to the cost of manufacturing the baskets. Moreover, the existing baskets may still have low fatigue resistance during use even after being subjected to multiple heat treatments.

What has been needed is a basket for an embolic protection device that is not prone to fracturing during manufacture or use, thereby reducing the need for heat treatment and improving fatigue resistance over conventional filter baskets. The present invention disclosed herein satisfies these and other needs.

SUMMARY OF THE INVENTION

The present invention is directed to an expandable basket for an embolic protection device used to filter embolic debris in a body lumen. In a preferred embodiment, the basket is comprised of a cylindrical body formed by a plurality of struts wherein adjacent struts are connected together at alternating ends in a zigzag pattern; an apex disposed at each of the connected ends of the struts; an internal radius at each apex; and a kerf formed in at least one strut extending from each internal radius toward an opposite end of the strut.

In one preferred embodiment, the apices at a first end of the cylindrical body are substantially longitudinally aligned, as are the apices at a second end of the cylindrical body. The invention may include optional undulating pattern of curves along a length of the struts to increase the flexibility of the struts. Another embodiment includes apices having a bulbous shape. The flattened bulbous shape preferably contours into the body of the struts. Also, in an alternative embodiment, adjacent apices are staggered longitudinally to permit the struts to fit together more compactly when the basket is in a compressed state.

In other alternative embodiments, the apices with a bulbous shape do not include the kerf adjacent the internal radii in the apices, but instead include struts having a smaller, constant cross-section. Moreover, the struts extending from the apices on one side of the basket are closer together than the struts extending from the apices on the opposite side of the basket. This pattern permits the struts to fit together even more compactly when compressed.

These and other advantages of the invention will become more apparent from the following detailed description of the invention when taken in conjunction with the accompanying exemplary drawings.

BRIEF DESCRIPTION OF THE DRAWINGS

FIG. 1a is a side elevational view of a pattern formed into tube stock for use in the present invention basket employed in an embolic protection device.

FIG. 1b is a plan view of the tube of FIG. 1a in which the tube has been unrolled and flattened into two dimensions to illustrate the strut pattern.

FIG. 1c is a perspective view of the basket from FIGS. 1a and 1b in the expanded state.

FIG. 2 is a plan view of an alternative embodiment tube for use as a basket in an embolic protection device, wherein the tube is unrolled and flattened into two dimensions revealing internal radii at the apices with respective kerfs extending from the radii.

FIG. 3 is a plan view of an alternative embodiment tube unrolled and flattened to depict an undulating wave formed into the struts.

FIG. 4 is a plan view of an alternative embodiment tube unrolled and flattened to depict staggered apices.

FIG. 5 is a plan view of an alternative embodiment tube unrolled and flattened to depict another strut pattern having more pronounced kerfs formed in the struts.

DETAILED DESCRIPTION OF THE PREFERRED EMBODIMENTS

The present invention is directed to a novel basket for use in an embolic protection device, wherein the basket includes structure that decreases stress concentrations in critical areas, and has a strut pattern that enables tighter compaction of the struts when the basket is in a compressed state. Turning now to the drawings, in which like reference numerals represent like or corresponding elements in the drawings, FIGS. 1a–1c illustrate a preferred embodiment basket 20 used in an embolic protection device (not shown).

In general, an embolic protection device filters embolic debris inside a body lumen. The embolic protection device is often used in the carotid artery during a stenting procedure in which the filter part of the device is deployed distal of the stent to capture friable embolic debris that might have been generated. Without such a filtering mechanism, the free floating embolic debris might cause a stroke in the patient during the procedure. After the procedure, the filter is collapsed to collect the debris, withdrawn into a recovery catheter, and removed from the patient's body.

FIG. 1a is a side elevational view of a preferred embodiment basket 20 in a compressed state. The basket 20 includes expandable struts 22 and strut arms 24 possessing spring-like or self-expanding properties and can move from a compressed or collapsed position as shown in FIG. 1a to an expanded or deployed position as shown in FIG. 1c. In FIG. 1c, the basket 20 includes a body composed of an elongated cylindrical component 25 having a first end 26 and a second end 27, a first truncated cone 28 that extends from the first end 26 of the cylindrical component 25, and a second truncated cone 30 that extends from the second end of the cylindrical component. The first truncated cone 28 terminates at a first hollow, cylindrical guide wire collar 32. Likewise, the second truncated cone 30 terminates at a second hollow, cylindrical guide wire collar 34.

Starting from the first collar 32, the expanded basket 20 includes a plurality of individual arms 24 that taper upward to form the first truncated cone 28 of the basket 20. The arms 24 merge with struts 22 that extend longitudinally to form the elongated, straight, center cylindrical component 25 of the basket 20. Individual arms 24 extend from the struts 22 and taper downward forming the second truncated cone 30 of the basket 20. The arms 24 of the second truncated cone 30 terminate at the second collar 34.

In a preferred embodiment, the basket 20 is manufactured in the unexpanded state from a small diameter hypotube 36, shown in FIG. 1a. The stock tubing used to make the basket 20 may be made of any biocompatible material, such as highly elastic stainless steel, a shape memory alloy such as nitinol, or the like. Of the shape memory or superelastic alloys, nitinol in the preferable range of 55% nickel-45% titanium is suitable. Typically, the preferred size tubing for making the present invention basket 20 in the compressed state has an outer diameter on the order of about 0.020–0.040 inch, with a wall thickness of about 0.003–0.006 inch. Of course, tubing size varies depending upon the application.

The basket 20 may be machined from seamless tubing. Alternatively, the tubing for the basket 20 may be formed by rolling flat, sheet stock into a tube where the seam is then welded. Rolled sheet stock which has been drawn through a circular die can also be used for the tubing.

The basket 20 has a strut pattern or framework that may be fashioned by several methods including electrical discharge machining (EDM) or chemical etching. A preferred method is to laser cut the hypotube 36. In this procedure, a computer controlled laser cuts away portions of the hypotube 36 following a pre-programmed template to form the desired pattern for the struts 22 and arms 24. Methods and equipment for laser machining small diameter tubing may be found in U.S. Pat. Nos. 5,759,192 and 5,780,807 to Saunders, whose contents are incorporated herein by reference.

After the strut pattern has been formed into the stock tubing, the basket 20 is deformed into expanded configurations. One method of expanding the basket 20 is by mechanically stretching it over a mandrel (not shown). The mandrel may incorporate pins to maintain the desired curvature of the struts 22 and arms 24. Because the preferred material is nitinol, once the desired expanded shape is set on the mandrel, the basket 20 is annealed at or above the martensite deformation temperature ($M_d$) of the material. This heat sets the new expanded shape into the basket 20. Annealing can be accomplished by heating the basket 20 within a variety of media such as air, molten salt, inert gas, or vacuum. Annealing at 500–550° C. is preferred for nickel—titanium alloys. After heat setting, the basket 20 is cleaned again. This process of deforming, annealing, and cleaning can be repeated until the desired expanded configuration is obtained. Naturally, the cost of producing the basket increases with each repetition of the process.

In an alternative embodiment, a basket may be formed from a tube (not shown) with a diameter that approximates the basket's size in the expanded configuration. In this configuration, the struts and arms are cut into the tube as they appear in the expanded configuration. This method eliminates the need to stretch and anneal the basket to achieve the expanded configuration. The basket may also be formed from a tube that is larger than the hypotube of FIG. 1a, but not as large as the expanded configuration. In this third configuration, the tube must still be expanded, but the tube does not require as many expansion increments as the basket made from the hypotube. The reduction or elimination of the expansion step reduces the time and cost of manufacturing the basket.

Referring again to FIG. 1c, the expanded basket 20 can be rotatably secured to a shaft member, such as a guide wire (not shown). The basket 20 is slidably mounted onto the guide wire by threading the guide wire into the first 32 and second 34 collars. The expandable basket 20 is mounted between a tapered fitting (not shown) located proximal to the first collar and a band (not shown) located distal to the second collar 34. This particular construction allows the expandable basket 20 to optionally rotate freely about the guide wire while allowing the basket to move longitudinally along the guide wire between the tapered fitting and the band. The above example is merely illustrative of one method of attaching the basket 20 to the guide wire. Other ways of attaching the basket 20 to the guide wire known in the art can be employed with the present invention.

By rotatably mounting the basket 20 to the guide wire in the manner described, the basket lengthens longitudinally with the second collar 34 sliding along the guide wire when the basket 20 is compressed for insertion into a delivery sheath (not shown). Likewise, the basket 20 contracts longitudinally while it self-expands radially upon release from the delivery sheath for deployment within the body lumen (not shown). An advantage of rotatably mounting the basket 20 on the guide wire is that the basket remains stationary if the guide wire is rotated at its proximal end after the basket has been deployed within the patient's vasculature. If the basket 20 were to rotate after deployment, the seal of the filter against the wall of the body vessel might be disturbed and possibly allow unfiltered blood to bypass the filter. Additionally, rotation of the basket 20 within a body vessel could cause trauma to the wall of the vessel.

Referring again to FIGS. 1a–1c, a strut pattern 44 is shown formed into the tube. Specifically, FIG. 1b is a plan view of the strut pattern 44 unrolled and flattened into two dimensions. The strut pattern 44 includes a plurality of struts 22 in the central cylindrical component 25 of the basket 20. The struts 22 are created by cutting slits 48 into the tube by the earlier described methods. The slits 48 alternate circumferentially with one slit starting from an opening 50 to the left of the first end 26 of the cylindrical component 25, thereby creating an open end 52, and extending longitudinally to a position prior to an opening 50 to the right of the second end 27 of the cylindrical component 25, thereby creating a closed end 54. The adjacent slit 48 on the circumference starts from an opening 50 to the right and extends longitudinally to a position prior to an opening 50 on the left. In this fashion, adjacent struts 22 are connected to each other at alternating ends.

When the tube expands (see FIG. 1c), the struts 22 formed by the slits open up and create a zigzag pattern 56 with apices 58 forming in the closed ends 54. Further, the apices 58 at the first end 26 of the cylindrical component 25 are optionally longitudinally aligned, as are the apices at the second end 27 of the cylindrical component. Between the openings 50 to the right and left sides of the struts 22 are the arms 24 that attach to the struts at the apices 58. The arms 24 extend longitudinally from the struts 22 to the collar 32, 34 at either end of the basket 20. The collars 32, 34 are portions of the tube that have not been cut longitudinally and are, therefore, not expandable. Alternatively, the collars 32, 34 can be separate from the basket 20 and the ends of the arms 24 can be coupled to the collars using bonding techniques that are known in the art, such as welding, brazing, and adhesive bonding.

With the slits 48 embodying substantially straight cuts, the expanded struts 22 form V's. Each V has an amplitude and a vertex, the latter coinciding with what has been identified as an apex 58. As seen in FIG. 1c, the apices 58 have small internal radii 60 at the internal portions of the closed ends 54. During expansion of the basket 20, the small internal radii 60 oftentimes experience a high concentration of stress that exceeds the ultimate stress of the material. Therefore, in order to expand the basket 20 without fracturing the struts 22 at the apices 58, the basket 20 is expanded in increments with each expansion increment followed by heat treatment to relieve the stress at the apices.

One approach to reducing the amount of stress in the internal radii 60 of the closed ends 54 of the struts 22 is to increase the size of the internal radii, thereby reducing the stress concentration factor. For example, FIG. 2 is a plan view of a strut pattern 62 flattened into two dimensions. This exemplary embodiment strut pattern 62 has closed ends or apices 64 of the struts 66 that feature enlarged internal radii 68. In addition, an optional kerf 70 extends from each enlarged internal radius 68 a distance towards the open end 72 of the slit 74. The kerf 70 further expands the radius, thereby reducing stress concentrations during expansion of the basket 76. By reducing the amount of stress in the basket 76, the number of incremental expansions and heat treatments can be reduced, thereby reducing the manufacturing cost of the baskets. Another benefit of reducing the amount of stress in the basket 76 is improved fatigue resistance. As the stress experienced by the basket 76 decreases, the number of cycles the basket can withstand prior to failure increases.

In addition to the enlarged internal radii 68 and kerfs 70 illustrated in FIG. 2, the stress within the internal radii can be further reduced, as shown in FIG. 3, by configuring the struts 78 with an undulating wave pattern of curves 80 along a length of the struts. The curves 80 create preferential bending points through a length of the struts 78, thereby effectively distributing the stress along the length of the struts rather than concentrating the stress at the internal radii where fractures typically occur. For example, when the strut pattern 62 of FIG. 2 is expanded, all of the displacement occurs at the internal radii 68. However, the struts 78 of FIG. 3 distribute this displacement among the various radii of the curves 80 within the wave pattern. Therefore, at any one curve 80 in FIG. 3, the strain is less than the strain experienced by the radius 68 of FIG. 2. Since stress and strain are linearly related, decreasing the strain in the radii of the curves 80 of FIG. 3 decreases the stress. Further, the undulating pattern of curves 80 reduces the amount of stress at any point along the length of the struts 78.

As seen in FIG. 4, another approach to relieving the stress in the internal radii 82, 84 of the apices 86, 88 is to longitudinally stagger or alternate the location of the apices on adjacent struts 90 of the basket 92. That is, one apex 86 is a first distance 94 from the collar 96 and the adjacent apex 88 on the circumference of the basket 92 is a second, farther distance 98 from the collar, with the distance from the collar to adjacent apices alternating between the first distance and the second distance. Another way to look at it is that the location of the apex 86 is staggered in the longitudinal direction relative to an adjacent apex 86. With staggered apices, there is more room in the same area of the strut pattern so that each apex 86 can have a larger radius, thereby reducing stress buildup.

For example, the apices 86, 88 in FIG. 4 are configured with a preferably flattened, bulbous shape having a radius larger than the apices 64 that are longitudinally aligned as in FIG. 2. In addition, the struts 90 are fashioned such that the apices 88 at the second distance 98 have their largest width at the same distance from the collar 96 as the smallest width of the apices 86 at the first distance 94. With the struts 90 including kerfs of removed material and the flattened bulbous shape of the apices 86, the end result is that the struts 90 fit together in a highly compact arrangement while in the compressed state, yet the stress at the key points is reduced during expansion.

FIG. 5 depicts another alternative embodiment basket 100 with apices 102, 104 having a flattened, bulbous shape. As with the basket 92 shown in FIG. 4, this alternative embodiment basket 100 includes apices 102, 104 that are longitudinally staggered. In addition, the apices 102, 104 shown in FIG. 5 curve inward, almost completing a circle, and contour into the length of the struts 106.

In this embodiment, the kerfs of the earlier described baskets are omitted. Rather, the cross sections of the struts 106 are reduced throughout. Further, as cut from a tube, the struts 106 extending from the apices 102 on the first end 108 of the cylindrical component 110 are closer together than the struts 106 extending from the apices 104 on the second end 112 of the cylindrical component.

The apices 102, 104 are configured with internal radii 114, 116 that are about the same size as those on the apices of baskets having the apices longitudinally aligned, as depicted in FIGS. 2 and 3. The flattened bulbous shape of the apices 102, 104 increases the internal radii 114, 116, thereby reducing the amount of stress within the internal radii. Also, the strut pattern of this basket 100 configuration enables the basket to be more highly compressed, thus allowing the basket to be easier to deliver within a patient.

In view of the foregoing, it is apparent that the systems of the present invention substantially enhance the efficiency of producing baskets for supporting embolic protection filters. Further modifications and improvements may additionally be made to the system disclosed herein without departing from the scope of the present invention. Accordingly, it is not intended that the invention be limited, except as by the appended claims.

What is claimed is:

1. An expandable filter basket for filtering embolic debris in a body lumen, the filter basket comprising:
    a cylindrical body formed with a plurality of slits to form a plurality of struts, wherein adjacent struts are connected together at alternating ends in a zigzag pattern;
    an apex disposed at each of the connected ends of the struts;
    an internal radius at each apex; and
    a kerf adjacent to each internal radius and formed in at least one strut extending toward the slit which forms the struts to reduce the width of at least one strut in the region adjacent to the internal radius.

2. The filter basket of claim 1, wherein:
    the apices at a first end of the cylindrical body are substantially longitudinally aligned; and
    the apices at a second end of the cylindrical body are substantially longitudinally aligned.

3. The filter basket of claim 1, wherein the struts include an undulating pattern of curves along a length of the struts created by undulating curved slits.

4. The filter basket of claim 1, wherein the apices include bulbous shapes.

5. The filter basket of claim 4, wherein the bulbous shapes contour into the struts.

6. The filter basket of claim 5, wherein
    adjacent apices at a first end of the cylindrical body are staggered longitudinally relative to each other; and
    adjacent apices at a second end of the cylindrical body are staggered longitudinally relative to each other.

7. The filter basket of claim 1, wherein the kerf is formed in both adjacent struts connected together to form the apex to reduce the width of both struts in the region adjacent to the internal radius.

8. The filter basket of claim 1, wherein each apex includes an external radius and the cylindrical body further includes additional struts, at least some of the apices being connected to one of these additional struts near the external radius.

9. The filter basket of claim 1, wherein the cylindrical body has an unexpanded state in which each kerf has a particular maximum width and the maximum width of each kerf is substantially the same width as the internal radius of the apex when placed in the unexpanded position.

10. The filter basket of claim 1, wherein the cylindrical body has an unexpanded state in which each kerf has a particular maximum width and the maximum width of each kerf is less than the width of the internal radius of the apex when placed in the unexpanded position.

11. A expandable filter basket for filtering embolic debris in a body lumen, the filter basket comprising:
    a cylindrical body having a plurality of slits which form a plurality of struts, wherein adjacent struts are connected together at alternating ends in a zigzag pattern;

an apex disposed at each of the connected ends of the struts, wherein one apex is staggered longitudinally relative to an adjacent apex to enable close packing of the struts when the basket is in a compressed state;

means for reducing stress at the apex; and means for distributing stress formed into the struts.

12. The filter basket of claim 11, wherein the means for distributing stress includes at least one strut having an undulating wave pattern formed by an undulating slit.

13. The filter basket of claim 12, wherein the struts include an undulating pattern along the lengths of the struts that are in phase.

14. The filter basket of claim 11, wherein the means for reducing stress at the apex includes at least one apex having an internal radius and a kerf extending therefrom away from the radius.

15. The filter basket of claim 11, wherein the apices include a flattened bulbous shape.

16. The filter basket of claim 11, wherein at least one apex includes a flattened bulbous shape that contours inward to provide space for an adjacent apex.

17. The filter basket of claim 11, wherein the basket includes open spaces in between the struts, and each strut includes a cross sectional area smaller than the open space.

18. A method for providing a expandable filter basket for filtering embolic debris in a body lumen, the filter basket comprising:

providing a cylindrical body;

cutting slits into the cylindrical body to form a plurality of struts;

forming the struts to connect at alternating ends to form a zigzag pattern;

providing an apex having a bulbous shape at each of the connected ends of the struts;

providing an internal radius at each apex; and cutting a kerf formed into the struts which extends from the internal radius towards the slit forming the struts to reduced the width of at least one strut in the area adjacent to the internal radius.

19. The method of claim 18, wherein the method includes contouring the bulbous shape into the struts.

20. The method of claim 19, wherein the method includes longitudinally staggering the adjacent apices.

21. A expandable filter basket for filtering embolic debris in a body lumen, the filter basket comprising:

a cylindrical body formed with a plurality of slits to create a plurality of struts connected together at alternating ends in a series of V-shapes;

an apex at each V-shape having a bulbous shape;

a radius formed inside the plurality of apices;

a kerf formed into the struts extending from the radius at the apices of the V-shapes toward the slit which forms the struts; and increased mass at a portion of the struts.

22. The filter basket of claim 21, wherein the struts include undulating waves along at least a portion thereof formed by undulating slits.

23. The filter basket of claim 21, wherein the basket includes a superelastic nickel—titanium alloy.

24. The filter basket of claim 21, wherein the basket includes a shape memory nickel—titanium alloy.

25. The filter basket of claim 21, wherein each apex includes an external radius and the cylindrical body further includes additional struts, at least some of the apices being connected to one of these additional struts at the external radius.

26. The filter basket of claim 21, wherein the cylindrical body has an unexpanded state in which each kerf has a particular maximum width and the maximum width of each kerf is substantially the same width as the internal radius of the apex when placed in the unexpanded position.

27. The filter basket of claim 21, wherein the cylindrical body has an unexpanded state in which each kerf has a particular maximum width and the maximum width of each kerf is less than the width of the internal radius of the apex when placed in the unexpanded position.

28. An expandable filter basket for filtering embolic debris in a body lumen, the filter basket comprising:

a body formed with a plurality of slits to create a plurality of struts, some of which are connected together;

an apex formed at the ends of the connected struts;

an internal radius at each apex; and a kerf formed at each apex along the internal radius extending toward and connecting with the slit which forms the struts.

29. The filter basket of claim 28, wherein the apex includes a bulbous shape.

30. The filter basket of claim 29, wherein the bulbous shapes contour into the struts.

31. The filter basket of claim 28, wherein a plurality of apices are formed on the body and are staggered longitudinally relative to each other.

32. The filter basket of claim 28, wherein some of the struts are connected together at alternating ends in a zigzag pattern.

33. The filter basket of claim 28, wherein the basket includes open spaces in between the struts, and each strut includes a cross sectional area smaller than the open space.

34. The filter basket of claim 28, wherein each apex includes an external radius and the cylindrical body further includes additional struts, at least some of the apices being connected to one of these struts at the external radius.

35. The filter basket of claim 28, wherein the cylindrical body has an unexpanded state in which each kerf has a particular maximum width and the maximum width of each kerf is substantially the same width as the internal radius of the apex when placed in the unexpanded position.

36. The filter basket of claim 28, wherein the cylindrical body has an unexpanded state in which each kerf has a particular maximum width and the maximum width of each kerf is less than the width of the internal radius of the apex when placed in the unexpanded position.

37. An expandable filter basket for filtering embolic debris in a body lumen, the filter basket comprising:

a cylindrical body formed with a plurality of slits to form a plurality of struts, wherein adjacent struts are connected together at alternating ends in a zigzag pattern, the zigzag pattern forming a proximal set of adjacent apices and a distal set of adjacent apices and adjacent proximal apices are staggered longitudinally relative to each other.

38. The filter basket of claim 37, wherein adjacent proximal apices are staggered longitudinally relative to each other.

39. The filter basket of claim 37, wherein the apices include bulbous shapes.

40. The filter basket of claim 37, further including:

an internal radius at each apex; and a kerf adjacent to each internal radius.

* * * * *

UNITED STATES PATENT AND TRADEMARK OFFICE
CERTIFICATE OF CORRECTION

PATENT NO. : 7,097,651 B2 Page 1 of 1
APPLICATION NO. : 09/948335
DATED : August 29, 2006
INVENTOR(S) : William J. Harrison et al.

It is certified that error appears in the above-identified patent and that said Letters Patent is hereby corrected as shown below:

Column 1,
Line 58, delete "titanum" and insert --titanium--.

Column 8,
Line 63, delete "A expandable" and insert --An expandable--.

Column 9,
Line 25, delete "a expandable" and insert --an expandable--.
Line 38, delete "reduced" and insert --reduce--.
Line 44, delete "A expandable" and insert --An expandable--.

Signed and Sealed this

Sixth Day of March, 2007

JON W. DUDAS
*Director of the United States Patent and Trademark Office*